United States Patent
Nishimura et al.

(10) Patent No.: US 7,223,775 B2
(45) Date of Patent: May 29, 2007

(54) STABILIZED ASCORBIC ACID DERIVATIVES

(75) Inventors: Norihito Nishimura, Kawasaki (JP); Hiroshi Ishii, Kawasaki (JP); Makoto Saito, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/510,756

(22) PCT Filed: Apr. 11, 2003

(86) PCT No.: PCT/JP03/04659

§ 371 (c)(1),
(2), (4) Date: Oct. 31, 2005

(87) PCT Pub. No.: WO03/086384

PCT Pub. Date: Oct. 23, 2003

(65) Prior Publication Data

US 2006/0100177 A1    May 11, 2006

Related U.S. Application Data

(60) Provisional application No. 60/373,609, filed on Apr. 19, 2002.

(30) Foreign Application Priority Data

Apr. 12, 2002    (JP)    ............................. 2002-110341

(51) Int. Cl.
| | | |
|---|---|---|
| A01N 43/42 | (2006.01) | |
| A01N 43/08 | (2006.01) | |
| A61K 31/47 | (2006.01) | |
| A61K 31/34 | (2006.01) | |
| C07F 9/06 | (2006.01) | |

(52) U.S. Cl. ........................ 514/313; 514/474; 549/222
(58) Field of Classification Search ................ 549/222; 514/99, 474, 313
See application file for complete search history.

(56) References Cited

U.S. PATENT DOCUMENTS

| 3,658,848 A | 4/1972 | Nomura et al. |
| 4,939,128 A | 7/1990 | Kato et al. |

FOREIGN PATENT DOCUMENTS

| EP | 0 875 246 A | 11/1998 |
| EP | 0 875 514 A | 11/1998 |
| EP | 1 074 242 A | 2/2001 |
| EP | 1 264 600 A | 12/2002 |
| JP | 52-18191 B | 5/1977 |
| JP | 58 222078 A | 12/1983 |
| JP | 61 050908 A | 3/1986 |
| JP | 61050908 | * 3/1986 |

OTHER PUBLICATIONS

International Search Report dated on Jul. 7, 2003.
Chinese Office Action dated Jan. 20, 2006.

* cited by examiner

*Primary Examiner*—Margaret D. Seaman
*Assistant Examiner*—Niloofar Rahmani
(74) *Attorney, Agent, or Firm*—Sughrue Mion, PLLC

(57) ABSTRACT

An ascorbic acid derivative, which is a compound represented by the following general formula (1) or a salt thereof: [Chemical Formula 11] (1)(wherein X and Y each represents H or a protective group for OH, $R_1$ and $R_2$ each represents an alkyl group having from 1 to 19 carbon atoms, which may be linear or branched, and the total number of carbon atoms in $R_1$ $R_2$ is an integer of 5 to 22).

13 Claims, No Drawings

STABILIZED ASCORBIC ACID DERIVATIVES

This Application claims the priority of an application based on U.S. Provisional Application Ser. No. 60/373609 (filed on Apr. 19, 2002).

TECHNICAL FIELD

The present invention relates to a novel ascorbic acid derivative. More specifically, the present invention relates to an ascorbic acid derivative which is a stable compound, and a process for producing the same. The present invention also relates to various forms or embodiments containing such an ascorbic acid derivative, such as vitamin C preparations or agents, collagen production accelerators, whitening agents, skin agent for external use or application, medical or pharmaceutical preparations, agricultural chemical preparations, animal or veterinary drug preparations, food additives and additives for animal feeding stuff, each containing an ascorbic acid derivative).

BACKGROUND ART

Ascorbic acid has activities such as inhibition of lipid peroxide production, acceleration of collagen production, retardation of melanin formation and enhancement of immune functions or performances. For these purposes, ascorbic acid has heretofore been used in the fields of medical or pharmaceutical preparations, agricultural chemical preparations, animal or veterinary drug preparations, foods, animal feeding stuff, cosmetic preparations, etc. However, ascorbic acid has poor stability with the elapse of time and poor lipid solubility. Accordingly, the amount of ascorbic acid which has permeated through the cell membrane and has cumulated in cells is rather limited, and the physiological actions of vitamin C cannot necessarily be achieved to a satisfactory extent, if the ascorbic acid per se is used. In order to improve the stability of ascorbic acid, various derivatives thereof have been proposed, such as one wherein the hydroxyl group present in the enediol portion at the 2- or 3-position, which is susceptible to oxidation, is converted into a phosphoric acid ester as described in, e.g., JP-B (examined Japanese patent publication) 52-1819 (Patent Document 1), and JP-A (unexamined published Japanese patent application) 02-279690 (Patent Document 2), or one wherein the acylation thereof is effected with a fatty acid so as to improve the lipid solubility, as described in, e.g., JP-A-59-170085 (Patent Document 3). However, there are very few derivatives which have been improved both in stability and in lipid solubility.

As for the ascorbic acid which has been improved both in stability and in lipid solubility, JP-A-61-152613 (Patent Document 4) describes a cosmetic composition containing a 6-O-higher-acyl ascorbic acid-2-phosphoric acid ester salt. However, in this patent publication, a process for producing a sulfuric acid ester (but not a phosphoric acid ester) thereof is described, a process for producing a phosphoric acid ester thereof is not described, and the ascorbic acid derivative, the provision of which is described in this publication, is not identified. From these points, it is difficult to recognize that the 6-O-higher-acyl ascorbic acid-2-phosphoric acid ester is disclosed in this publication so as enable the practice thereof.

JP-A-10-298174 (Patent Document 5) describes a process for producing 6-O-higher-acyl ascorbic acid-2-phosphoric acid ester and results of the structure determination of the substance. It is stated that the 6-O-higher-acyl ascorbic acid-2-phosphoric acid ester produced by this process is improved both in stability and in lipid solubility, and the uptake thereof into cells is facilitated. However, among these substances, ascorbic acid-2-phosphoric acid ester-6-palmitatic acid ester sodium salt and an aqueous solution thereof are not yet satisfactory in view of the stability thereof.

Patent Document 1: JP-B-52-1819
Patent Document 2: JP-A-02-279690
Patent Document 3: JP-A-59-170085
Patent Document 4: JP-A-61-152613
Patent Document 5: JP-A-10-298174

DISCLOSURE OF INVENTION

An object of the present invention is to provide an ascorbic acid derivative which has solved the above-mentioned problems encountered in the prior art, and a process for producing such an ascorbic acid derivative.

Another object of the present invention is to provide a 6-O-higher-acyl ascorbic acid-2-phosphoric acid ester and/or a salt thereof which have been improved in stability and have a novel structure, a process for producing the same, and a proparataion (such as cosmetic material) using the 6-O-higher-acyl ascorbic acid-2-phosphoric acid ester and/or a salt thereof.

As a result of earnest study, the present inventors have found that newly synthesized 6-O-higher-acyl ascorbic acid-2-phosphoric acid esters and/or salts thereof wherein the acyl group (fatty acid residue) at the 6-position thereof is branched at the α-position have greatly improved in the stability thereof, as compared with conventional 6-O-higher-acyl ascorbic acid-2-phosphoric acid esters having a linear fatty acid residue and/or salts thereof. The present invention has been accomplished based on this discovery.

The ascorbic acid derivative according to the present invention represented by the general general formula (1) is characterized in that the higher fatty acid ester at the 6-position is a fatty acid ester branched at the α-carbon.

According to the present inventors' experiments, it has been found that the ester bond of the conventional 6-O-higher linear fatty acid esters is decomposed or cloven during the storage thereof so as to cause a reduction in the ratio of the ascorbic acid-2-phosphoric acid ester remaining after the storage. On the contrary, the ascorbic acid-2-phosphoric acid-6-fatty acid ester according to the present invention has an improved stability. According to the present inventors' investigation and knowledge, it is presumed that the fatty acid ester (such as ascorbic acid-2-phosphoric acid-6-fatty acid ester which has been synthesized from a fatty acid branched at the α carbon, as a starting material has a reinforced or strengthened ester bond.

More specifically, the present invention relates to the following matters.

[1] An ascorbic acid derivative, which is a compound represented by the following general formula (1) or a salt thereof:

[Chemical Formula 1]

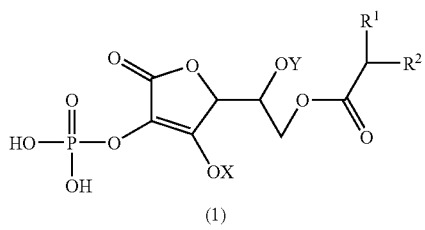

(1)

(wherein X and Y each represents H or a protective group for OH, $R^1$ and $R^2$ each represents an alkyl group having from 1 to 19 carbon atoms, which may be linear or branched, and the total number of carbon atoms in $R^1$ and $R^2$ is an integer of 5 to 22).

[1] The ascorbic acid derivative according to [1], which is a salt with one or more metal selected from the group consisting of alkali metal, alkaline earth metal, aluminum, iron, zinc and bismuth.

[3] The ascorbic acid derivative according to [1], which is a salt with ammonia, monoethanolamine, diethanolamine, triethanolamine, dicyclohexylamine or 2-amino-1-methylpropanol.

[4] The ascorbic acid derivative according to any one of [1] to [3], wherein the total number of carbon atoms in $R^1$ and $R^2$ of the general formula (1) is an integer of 8 to 18.

[5] The ascorbic acid derivative according to [4], wherein $R^1$ and $R^2$ of the general formula (1) are a linear alkyl group, and the total number of carbon atoms in the linear alkyl groups of $R^1$ and $R^2$ is 14 or 16.

[6] The ascorbic acid derivative according to [5], wherein in the general formula (1), $R^1$ is n-$C_9H_{19}$ and $R^2$ is n-$C_7H_{15}$; or $R^1$ is n-$C_8H_{17}$ and $R^2$ is n-$C_6H_{13}$.

[7] A process for producing an ascorbic acid derivative according to any one of [1] to [6], comprising a step of reacting a compound represented by the following general formula (2) and/or a salt thereof:

[Chemical Formula 2]

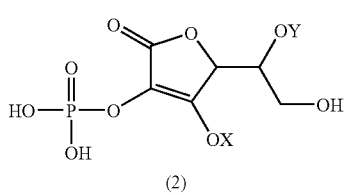

(2)

(wherein X and Y each represents H or a protective group for OH), with at least one selected from fatty acid, fatty acid salt, fatty acid ester, fatty acid halide, and/or fatty acid anhydride.

[8] The process for producing an ascorbic acid derivative according to [7], wherein the reaction is performed in the presence of a condensing agent and/or dehydrating agent.

[9] The process for producing an ascorbic acid derivative according to [8], wherein the dehydrating agent is sulfuric acid.

[10] The process for producing an ascorbic acid derivative according to any one of [7] to [9], wherein the reaction is conducted in a solvent selected from the group consisting of: water, acetone, dioxane, toluene, ethylbenzene, methyl-tert-butyl ether, and sulfuric acid.

[11] A vitamin C preparation comprising the ascorbic acid derivative according to any one of [1] to [6] as an effective ingredient.

[12] A collagen production accelerator comprising the ascorbic acid derivative according to any one of [1] to [6] as an effective ingredient.

[13] A whitening preparation comprising the ascorbic acid derivative according to any one of [1] to [6] as an effective ingredient.

[14] A skin preparation for external use, comprising the ascorbic acid derivative according to any one of [1] to [6] as an effective ingredient.

[15] The skin preparation for external use according to [14], which contains an ascorbic acid-2-phosphoric acid ester and/or a salt thereof.

[16] The skin preparation for external use according to [14], which contains sodium salt, potassium salt, magnesium salt or zinc salt of the ascorbic acid-2-phosphoric acid ester.

[17] A cosmetic material comprising the skin preparation for external use according to any one of [14] to [16].

[18] A composition comprising the ascorbic acid derivative d according to any one of [1] to [6], in the form of a medical or pharmaceutical preparation, an agrochemical preparation or an animal drug preparation.

[19] A composition comprising the ascorbic acid derivative according to any one of [1] to [6], in the form of a food or feed additive.

BEST MODE FOR CARRYING OUT THE INVENTION

Hereinbelow, the present invention will be described in detail with reference to the accompanying drawings as desired. In the following description, "%" and "part(s)" representing a quantitative proportion or ratio are those based on mass, unless otherwise noted specifically.

(Ascorbic Acid Derivative)

The ascorbic acid derivative according to the present invention is a compound represented by the following general formula (1) and/or a salt thereof:

[Chemical Formula 3]

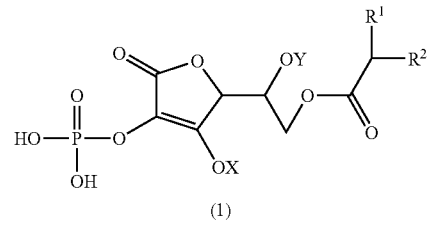

(1)

(wherein X and Y each represents H or a protective group for OH, $R^1$ and $R^2$ each represents an alkyl group having from 1 to 19 carbon atoms, which may be linear or branched, and the total number of carbon atoms in $R^1$ and $R^2$ is an integer of 5 to 22).

In the present invention, unless otherwise noted specifically, the ascorbic acid or ascorbic acid derivative may preferably be an L-form.

The ascorbic acid derivative according to the present invention is less liable to be oxidized and has an excellent stability, because the 2-position of the ascorbic acid is esterified into a phosphoric acid ester.

Further, in the ascorbic acid derivative according to the present invention, the 6-position thereof is esterified into a higher fatty acid ester, and therefore, this compound can have an appropriate lipid solubility, and has a characteristic such that the uptake thereof into cells is facilitated. In addition, the phosphoric acid group at the 2-position in this compound is readily hydrolyzed by phosphatase in a living body and the higher fatty acid ester at the 6-position is an ester with a primary alcohol (6-position) which is susceptible to the action of lipase or esterase, this compound may easily be converted into ascorbic acid in a living body.

(Production Process-1 for Ascorbic Acid Derivative)

The compound represented by the general formula (1) and/or a salt according to the present invention can be produced, for example, according to the following reaction formula:

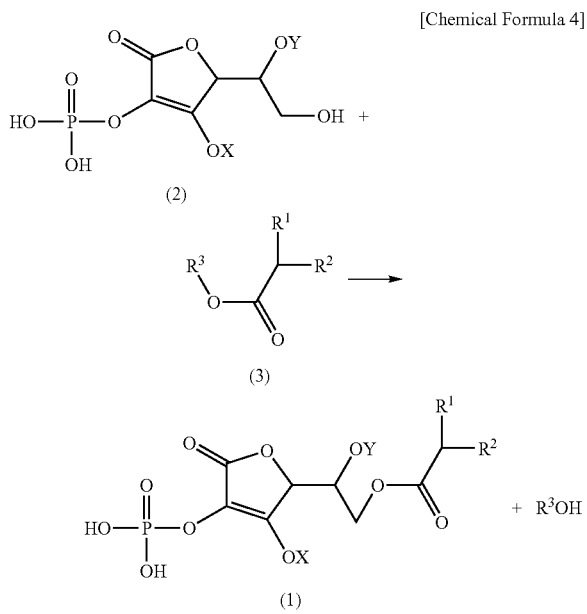

[Chemical Formula 4]

(wherein X and Y each represents H or a protective group for OH, $R^1$ and $R^2$ each represents an alkyl group having from 1 to 19 carbon atoms, the total number of carbon atoms in $R^1$ and $R^2$ is from 5 to 22, and $R^3$ represents a hydrogen atom, a cation or an alkyl group having from 1 to 5 carbon atoms).

More specifically, a compound represented by the formula (2) and/or a salt thereof is reacted with at least one of a fatty acid branched at the α carbon represented by the formula (3), and an ester and a salt thereof, to produce an ascorbic acid-2-phosphoric acid-6-fatty acid ester (1) and/or a salt thereof.

(Dehydrating or Condensing Agent)

The above-described reaction may preferably be performed in the presence of a dehydrating or condensing agent.

The dehydrating or condensing agent to be used in such a case is not particularly limited. Preferred examples of the condensing agent may include: N,N'-dicyclohexyl carbodiimide, N,N'-diisopropyl carbodiimide, N-ethyl-N'-3-dimethylaminopropyl carbodiimide, benztriazole-1-yl-tris(dimethylamino)phosphonium hexafluorophosphide salt, diphenylphosphoryl azide for optimum as condensing agent. Among these, it is preferred to use N,N'-diisopropylcarbodiimide. Preferred examples of the dehydrating agent may include: phosphorus pentoxide, solid phosphoric acid, a titanium oxide, an alumina and a sulfuric acid. Among these, it is preferred that sulfuric acid (preferably, concentrated sulfuric acid of 95 mass % or more) is used, and the concentrated sulfuric acid, an ascorbic acid-2-phosphoric acid ester salt and a fatty acid or an ester or salt thereof are mixed and reacted.

In the fatty acid ester of the formula (3), $R^3$ represents an alkyl ester having from 1 to 5 carbon atoms, and may preferably be a lower alkyl ester having from 1 to 3 carbon atoms, more preferably a methyl ester or an ethyl ester.

The reaction time and the reaction temperature may vary depending on whether the fatty acid is a free acid, an ester or a salt, or on the kind and amount of the condensing agent. However, the reaction time may generally be from 1 to 120 hours, preferably from 4 to 10 hours, and the reaction temperature may generally be from 5 to 70° C., preferably from 30 to 50° C.

The water content to be carried over from the starting materials or catalyst into the-reaction solution may suitably be 10% or less, preferably 2% or less.

(Solvent)

when a solvent is used in this reaction, sulfuric acid per se as a condensing agent can also be used as the solvent. Alternatively, it is also possible to select the solvent from other solvents capable of dissolving the starting materials. Specific examples of such other solvents may include: water, acetone, dioxane, toluene, ethylbenzene and methyl-tert-butyl ether, etc.

(Production Process-2 for Ascorbic Acid Derivative)

The compound represented by the general formula (1) and/or a salt according to the present invention can also be produced, for example, according to the following reaction formula:

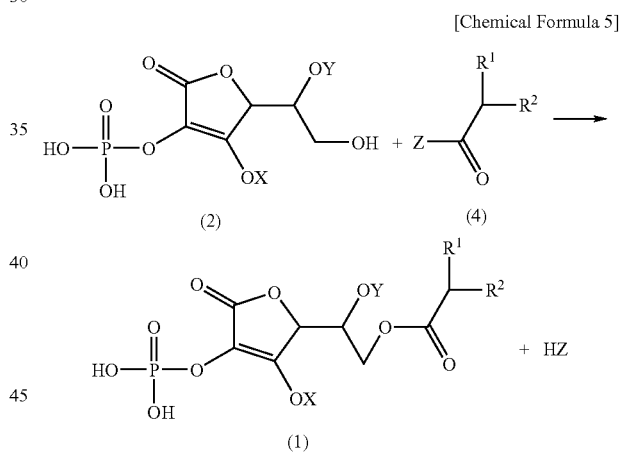

[Chemical Formula 5]

(wherein X and Y each represents H or a protective group for OH, $R^1$ and $R^2$ each represents an alkyl group having from 1 to 19 carbon atoms, the total number of carbon atoms in $R^1$ and $R^2$ is from 5 to 22, and Z represents a halide).

More specifically, an ascorbic acid-2-phosphoric acid represented by the general formula (2) and/or a salt thereof is reacted with a fatty acid halide branched at the α carbon represented by the general formula (4) to produce an ascorbic acid-2-phosphoric acid-6-fatty acid ester (1) and/or a salt thereof.

(Base)

The above-described reaction may preferably be performed in the presence of a base. The base is not particularly limited, as long as it is a base which is usually usable as a dehydrohalogenating agent in the reaction of an alcohol with an acid halide. Preferred examples thereof may include tertiary amines such as pyridine and triethylamine.

(Production Process-3 for Ascorbic Acid Derivative)

The compound represented by the general formula (1) and/or a salt thereof can also be produced, for example, according to the following reaction formula:

[Chemical Formula 6]

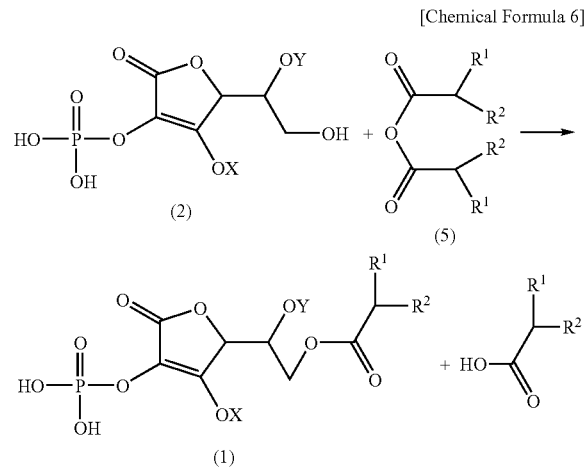

(wherein X and Y each represents H or a protective group for OH, $R^1$ and $R^2$ each represents an alkyl group having from 1 to 19 carbon atoms, and the total number of carbon atoms in $R^1$ and $R^2$ is from 5 to 22).

More specifically, a fatty acid anhydride branched at the α carbon represented by the formula (5) is reacted with an ascorbic acid-2-phosphoric acid represented by the general formula (2) and/or a salt thereof, to produce an ascorbic acid-2-phosphoric acid-6-fatty acid ester represented by the formula (1) and/or a salt thereof.

(Mole Ratio)

In the production process according to the present invention, the starting materials may be used in equimolar amounts in any of the above-mentioned reactions. However, it is possible to use either one of the starting materials may be present in slight excess (e.g., either one of the starting materials may be present in about 1.0–3.0, more preferably about 1.0–1.5 in terms of the mole ratio therebetween), as long as substantially no problem arises during the purification or isolation to be effected after the predetermined reaction.

(Purification and/or Isolation)

The purification or isolation method is not particularly limited. More specifically, the purification or isolation may be performed by using a general method such as solvent extraction, washing, salting out or column chromatography. For example, the reaction product may be isolated or purified by ether extraction or washing with non-polar solvent such as hexane. If desired, the thus obtained product may further be purified by reverse phase chromatography or the like.

Both of the group represented by X and Y at the 3- and 5-positions of the ascorbic acid of the formula (2) may preferably be H. However, in any of the above-mentioned reactions, these groups may be substituted by a protective group which is not substantially affected by the reaction.

<Specific Examples of Non-Susceptible Protective Group> acyl group, alkanesulphonyl group, benzenesulphonyl group which may be substituted, dialkyl carbamoyl group, benzyl group, alkyl group, silyl group (Salt of Ascorbic Acid Derivative)

The salt of the compound represented by the following general formula (1) may be obtained in the following manner:

[Chemical Formula 7]

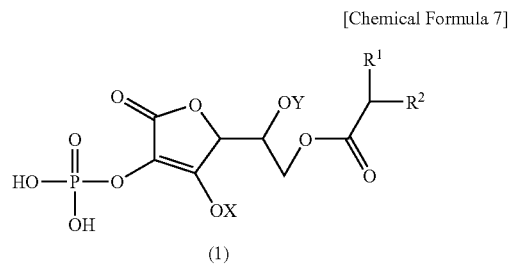

(wherein X and Y each represents H or a protective group for OH, $R^1$ and $R^2$ each represents an alkyl group having from 1 to 19 carbon atoms, which may be linear or branched, and the total number of carbon atoms in $R^1$ and $R^2$ is an integer of 5 to 22)

Thus, the obtained ascorbic acid-2-phosphoric acid-6-higher fatty acid ester is, for example, neutralized with an appropriate base (for example, sodium hydroxide, potassium hydroxide, magnesium oxide, calcium hydroxide, ammonia, monoethanolamine, diethanolamine, triethanolamine or dicyclohexylamine) in a solvent capable of dissolving the ester, such as water or methanol, whereby a salt with the base can be obtained.

The kind of the salt of ascorbic acid derivative is not particularly limited, as long as the usage or application of the salt of ascorbic acid derivative is not substantially impaired. In view of easy availability, and compounding thereof into formulations, the salt may preferably be those containing alkali metals, alkaline earth metals, aluminum, iron, zinc and bismuth. Among these, preferred are alkali metals such as sodium and potassium, and alkaline earth metals such as calcium and magnesium. These may be used individually or in combination of two or more species thereof.

(Protection of Hydroxyl Group)

In the compound represented by the above general formula (1), the hydroxyl group at 3- or 5-position can also be protected by a conventionally known group which is readily converted into a hydroxyl group. The present invention may include compounds having such a protective group (for example, acyl group, alkanesulfonyl group, a benzenesulfonyl group which may be substituted, or dialkylcarbamoyl group, benzyl group, alkyl group, silyl group, etc.). The protective group may be introduced into the predetermined compound, before or after the esterification reaction at the 6-position.

This reaction can be applied not only to the process for producing a 6-O-higher fatty acid ester of ascorbic acid-2-phosphoric acid according to the present invention, but also to the production of a conventionally known 6-O-lower fatty acid ester wherein $R^1$ and $R^2$ in the above general formula (1) each independently represents $CH_3$ or $C_2H_5$.

(Preparation)

The ascorbic acid derivative according to the present invention exhibits a vitamin C activity which has remarkably been improved both in stability and in lipid solubility, as compared with those of conventionally known ascorbic acid derivatives. Accordingly, vitamin C can be supplied by the ascorbic acid derivative according to the present invention per se, or by a preparation (vitamin C preparation) containing the ascorbic acid derivative according to the present invention. The usage or application of the ascorbic acid derivative according to the present invention is not particularly limited. For example, vitamin C can be effectively supplied when the ascorbic acid derivative according to the present invention is blended in medical or pharmaceutical preparations, agricultural chemicals, foods, feeds or cosmetic preparations, etc.

(Higher Fatty Acid Ester)

The ascorbic acid derivative according to the present invention may suitably be L-form in view of the vitamin C activity thereof. Further, the higher fatty acid ester at the 6-position is characterized in that it is a fatty acid ester branched at the α carbon. As described above, according to the present inventors' experiment, it has been found that the ester bond of conventional 6-O-higher linear fatty acid esters are decomposed or cloven during the storage thereof to cause a reduction in the ratio of an ascorbic acid-2-phosphoric acid ester remaining after the storage. On the contrary, it is presumed that in the ascorbic acid derivative according to the present invention (e.g., an ascorbic acid-2-phosphoric acid-6-fatty acid ester which has been synthesized from a fatty acid branched at the α carbon), the ester bond is reinforced or strengthened, and therefore the ascorbic acid derivative according to the present invention shows an improved stability in a stability test.

In view of the lipid solubility, preferred examples of the 6-O-higher fatty acid ester may include 2-butylhexanoic acid ester, 2-hexyldecanoic acid ester and 2-heptylundecylic acid ester.

(Collagen Production Accelerator, External Skin Agent, etc.)

The ascorbic acid derivative obtained by the production process according to the present invention has a collagen production accelerating effect and a whitening effect and therefore, it can also be used as a collagen production accelerator or a whitening agent. Further, the ascorbic acid derivative can be effectively used as a skin agent for external application, for example, by formulating it with another skin agent.

When the ascorbic acid derivative is used as a skin agent, the skin agent for external application according to the present invention may contain an ascorbic acid-2-phosphoric acid ester represented by the following general formula (2) and/or a salt thereof, in addition to the ascorbic acid derivative (represented by the general formula (1)) obtained by the production process according to the present invention:

[Chemical Formula 8]

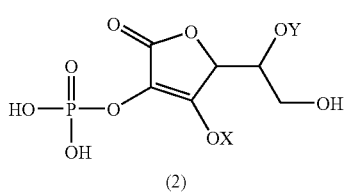

(2)

(wherein X and Y each represents H or a protective group for OH). In an embodiment wherein the ascorbic acid-2-phosphoric acid ester represented by the following general formula (2) and/or a salt thereof is contained, it also is possible to achieve an advantageous effect of providing an ascorbic acid source to both of epidermis (or cuticle) and dermis (or corium).

(Ascorbic Acid-2-Phosphoric Acid Ester)

Hereinbelow, the ascorbic acid-2-phosphoric acid ester and/or a salt thereof are described in more detail.

The ascorbic acid-2-phosphoric acid ester according to the present invention may be any one of D-form, L-form and DL-form, but may preferably be L-form. The salt of the ascorbic acid-2-phosphoric acid ester may be, for example, a compound wherein a phosphoric acid ester is bonded to the 2-position of the ascorbic acid, and the phosphoric acid group of the phosphoric acid ester forms a salt with a base.

Specific examples of the salt of ascorbic acid-2-phosphoric acid ester may include: alkali metal salt, alkaline earth metal salt, Zn salt, Al salt, Ti salt, etc. Among these, in an economical point of view, preferred are Na salt, K salt, Mg salt and Zn salt, and more preferred are Na salt and Mg salt.

(Collagen Production Accelerating Effect)

In the present invention, the collagen production accelerating effect means that when the hydroxyproline content, for example, in skin tissue is measured by an amino acid analysis method and the thus obtained data is used as an index of collagen production accelerating effect, the hydroxyproline amount in the test area (or segment) is at least 1.2 to 2 times that in the control area.

In the present invention, the collagen production accelerator, the whitening agent or the skin agent for external application can be used while the effect thereof per se is emphasized as a main effect. However, it is also possible to further add another ingredient thereto so as to modify or adjust the effect.

In the collagen production accelerator, whitening agent or skin agent for external application, the amount of the ascorbic acid derivative obtained by the production process according to the present invention which has been blended into these preparations may appropriately be selected in view of the degree of the desired effect or the relationship with other ingredients to be used in combination therewith. However, it may be, for example, from 0.01 to 30% by mass, preferably from 0.03 to 20% by mass, based on the entire amount of the preparation.

In order to make use of the collagen production accelerating effect and/or the whitening effect, another additive (e.g., known ingredient effective against aging of skin, known ingredient effective in accelerating the collagen production and suppressing wrinkle, known whitening agents, etc.) may be added.

It is possible to blend as such an additive, those such as tea extract, t-AMCHA, L-lysine, L-arginine, caffeine, tannin, verapamil, tranexamic acid, tranexamic acid derivative, hyaluronic acid, glycyrrhiza extract, glabridin, hydrothermal extracts of fruits such as quince, raspberry and avocado, white wine yeast extract, various Japanese and Chinese crude drugs or extracts thereof, aroma extract, tocopherol acetate, glycyrrhizic acid, glycyrrhizic acid derivatives, arbutin, koji (or malt), glucose, fructose, mannose, sucrose, trehalose, phytoglycogen, retinoic acid, retinol, retinol acetate and retinol palmitate.

A biologically active substance to be described later, which can be used as a whitening agent, may also be used in combination.

Also, various base ingredients can be added according to the dosage form or shape of the skin agent for external application.

Such a base ingredient can be added according to various specific usage, applications or purposes. Specific examples of the base ingredient may include: liquid oils and fats, solid oils and fats, waxes, ester oil, hydrocarbon oil, silicone resin, silicone, anionic surfactant, anion-type surfactant, cationic surfactant, amphoteric surfactant, nonionic surfactant, lower alcohol, sterols, water-soluble polymer, sequestering agent (e.g., disodium edetate, trisodium edetate, sodium citrate, sodium polyphosphate, sodium metaphosphate, gluconic acid), neutralizer, pH adjusting agent, bactericide or anti-fungus agent, and perfume.

In a case where the ascorbic acid of the present invention is applied to skin, another ingredient which is generally usable in skin preparations can be blended, as long as such addition does not substantially impair the effect of the present invention. Specific examples of the ingredient to be used may include: medicaments, agents, drugs, medicines, mediums, pharmaceuticals, pharmaceutical preparations as described in *Japanese Standards of Cosmetic Ingredients* (*JSCI*), *2nd Edition, Annotation*, compiled by Nippon Koteisho Kyokai, issued by Yakuji Nippo, Ltd. (1984), *Specifications of Ingredient Other Than Those Listed in JSCI*, supervised by Examination Division, Pharmaceutical Affairs Bureau, Ministry of Health and Welfare, issued by Yakuji Nippo, Ltd. (1993), *Specifications of Ingredient Other Than Those Listed in JSCI, Supplement*, supervised by Examination Division, Pharmaceutical Affairs Bureau, Ministry of Health and Welfare, issued by Yakuji Nippo, Ltd. (1993), *The Comprehensive Licensing Standards of Cosmetics by Category*, supervised by Examination Division, Pharmaceutical Affairs Bureau, Ministry of Health and Welfare, issued by Yakuji Nippo, Ltd. (1993), and *Kesho-hin Genryo Jiten* (*Handbook of Cosmetic Ingredients*), Nikko Chemicals (1991), etc.

Specific examples of the materials or agents which can be added to the preparation according to the present invention will be enumerated below. These examples include, e.g., oil, higher alcohol, fatty acid, ultraviolet absorber, powder, pigment, surfactant, polyhydric alcohol and sugar, polymer, biologically active ingredient, solvent, antioxidant, perfume and antiseptic. However, as a matter of course, those usable in the present invention are not limited to these examples.

(1) Specific Examples of Oil (Ester-Type Oil Phase Ingredient)

Triglyceryl 2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, isoarachyl neopentanoate, caprylic-capric acid triglyceride, trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol di(caprylate/caprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin oleate, polyglycerin isostearate, dipropyl carbonate, dialkyl carbonate (C12-18), triisocetyl citrate, triisoarachyl citrate, triisooctyl citrate, lauryl lactate, myristyl lactate, cetyl lactate, octyldecyl lactate, triethyl citrate, acetyltriethyl citrate, acetyltributyl citrate,-trioctyl citrate, diisostearyl malate, 2-ethylhexyl hydroxystearate, 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate and isostearyl 12-stearoylhydroxystearate.

(Hydrocarbon-Type Oil Phase Ingredient)

Squalane, liquid paraffin, α-olefin oligomer, isoparaffin, ceresin, paraffin, liquid isoparaffin, polybutene, microcrystalline wax and petrolatum.

(Animal and Plant Oil, Hardened Oil Thereof, and Wax of Natural Origin)

Animal oils and hardened oils thereof, such as beef tallow, hardened beef tallow, lard, hardened lard, horse oil, hardened horse oil, mink oil, orange roughy oil, fish oil, hardened fish oil and egg yolk oil; plant oils and hardened oils thereof such as avocado oil, almond oil, olive oil, cacao oil, apricot kernel oil, coconut oil, sesame oil, wheat germ oil, rice germ oil, rice bran oil, safflower oil, shea butter, soybean oil, evening primrose oil, tsubaki oil, corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil; and waxes such as beeswax, high acid number beeswax, lanolin, reduced lanolin, liquid lanolin, carnauba wax and montan wax.

(Silicone-Type Oil Phase Ingredient)

Dimethylpolysiloxane, methylphenylpolysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxane•methylcetyloxysiloxane copolymer, dimethylsiloxane•methylstearoxysiloxane copolymer, alkyl-modified organopolysiloxane, terminal-modified organopolysiloxane, dimethiconol, silicone gel, acryl silicone, trimethylsiloxysilicic acid and silicone RTV rubber.

(Fluorine-Type Oil Phase Ingredient)

Perfluoropolyether, fluorine-modified organopolysiloxane, fluorinated pitch, fluorocarbon, fluoroalcohol and fluoroalkyl polyoxyalkylene-comodified organopolysiloxane.

(2) Specific Examles of Higher Alcohol

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol.

(3) Specific Examples of Fatty Acid

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid and 2-ethylhexanoic acid.

(4) Specific Examples of Ultraviolet Absorber

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, octyl para-methoxycinnamate, 2-ethylhexyl para-methoxycinnamate, glyceryl mono-2-ethyl hexanoate di-para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenonedisulfonate, dihydroxybenzophenone, dihydroxydimethoxybenzophenone, hydroxyoctoxybenzophenone, tetrahydroxybenzophenone, butylmethoxydibenzoylmethane, 2,4,6-trianilino-p-(carbo-2-ethylhexyl-1-oxy)-1,3,5-triazine, 2-(2-hydroxy-5-methylphenyl)benzotriazole, methyl-O-aminobenzoate, 2-ethylhexyl-2cyano-3,3-diphenylacrylate, phenylbenzimidazole sulfuric acid, 3-(4-methylbenzylidene)camphor, isopropyldibenzoylmethane, 2-ethylhexyl 4-(3,4-dimethoxyphenylmethylene)-2,5-dioxy-1-imidazolidinepropionate, and polymer derivatives and silane derivatives thereof.

(5) Specific Examples of Powder and Pigment

Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride. The shape (e.g., sphere, bar, needle, plate, amorphous, scale, spindle) and the particle size of these powders are not particularly limited.

These powders may or may not be previously surface-treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment.

(6) Specific Examples of Surfactant (Anionic Surfactant)

Fatty acid soap, α-acyl sulfonate, alkyl sulfonate, alkylallyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt and perfluoroalkylphosphoric acid ester.

(Cationic Surfactant)

Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylamide stearate, dimethylaminopropylamide stearate and lanolin derivative quaternary ammonium salt.

(Amphoteric Surfactant)

Carboxybetaine type, amidobetaine type, sulfobetaine type, hydroxysulfobetaine type, amidosulfobetaine type, phosphobetaine type, aminocarboxylate type, imidazoline derivative type and amidoamine type.

(Nonionic Surfactant)

Propylene glycol fatty acid ester, glycerin fatty acid ester, polyglycerin fatty acid ester, sorbitan fatty acid ester, POE sorbitan fatty acid ester, POE sorbitol fatty acid ester, POE glycerin fatty acid ester, POE alkyl ether, POE fatty acid ester, POE hydrogenated castor oil, POE castor oil, POE•POP copolymer, POE•POP alkyl ether, polyether-modified silicone lauric acid alkanolamide, alkylamine oxide and hydrogenated soybean phospholipid.

(Natural-Type Surfactant)

Lecithin, saponin and sugar-type surfactant.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1,3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose and pullulan. Chemically modified products thereof can also be used.

(8) Specific Examples of Polymer Compound

Anionic polymer compounds such as acrylic acid ester/methacrylic acid ester copolymer (PLUS-SIZE, produced by Go'o Kagaku K.K.), vinyl acetate/crotonic acid copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/acrylate copolymer (RUBIFLEX, produced by BASF), acrylate/acrylamide copolymer (ULTRAHOLD, produced by BASF), vinyl acetate/butyl maleate•isobornyl acrylate copolymer (ADVANTAGE, produced by ISP), carboxy vinyl polymer (CARBOPOL, produced by BF Goodrich) and acrylic acid•alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylaminoethyl methacrylate copolymer (AMPHOMER, produced by NSC); cationic polymer compounds such as quaternized compound of vinylpyrrolidone/dimethylaminoethyl methacrylate copolymer (GAFQUAT, produced by ISP) and methyl vinyl imidazolium chloride/vinylpyrrolidone copolymer (RUBICOTE, produced by BASF); and nonionic polymer compounds such as polyvinylpyrrolidone/ vinyl acetate copolymer (RUBISCOL VA, produced by BASF) and vinylpyrrolidone/dimethylaminoethyl methacrylate copolymer (COPOLYMER VC713, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabi, crystal cellulose, arabino galactan, karaya gum, tragacanth gum, alginic acid, albumin, casein, cardrun, gellan gum and dextran, can also be suitably used.

(9) Specific Examples of Biologically Active Ingredient

The biologically active ingredient may include substances which are capable of imparting some biological activity to skin, when such a substance is applied to the skin. Specific examples thereof may include: whitening ingredient, anti-inflammatory, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: angelica extract, avocado extract, hydrangea extract, althea extract, arnica extract, aloe extract, apricot extract, apricot core extract, ginkgo extract, fennel extract, turmeric extract, oolong tea extract, rose fruit extract, echinacea leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, sabdariffa extract, pyracantha fortuneana fruit extract, kiwi extract, cinchona extract, cucumber extract, guanosine, gardenia extract, sasa albo-marginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, salvia extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, hibiscus sabdariffa flower extract, ophiopogon tuber extract, parsley extract, honey, witch hazel extract, pellitory extract, isodonis extract, matricaria extract, loquat extract, coltsfoot extract, butterbur scape extract, Poria cocos extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, citrus extract, coix seed extract, mugwort extract, lavender extract, apple extract, lettuce extract, lemon extract, Chinese milk vetch extract, rose extract, rosemary extract, Roman chamomile extract and royal jelly extract.

Other examples may include biopolymers such as deoxyribonucleic acid, mucopolysaccharide, sodium hyaluronate, sodium chondroitin sulfate, collagen, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory such as $\epsilon$-aminocaproic acid, glycyrrhizic acid, $\beta$-glycyrrhetic acid, lysozyme chloride, guaiazlene and hydrocortisone;

vitamins such as vitamin A, vitamin $B_2$, vitamin $B_6$, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as $\alpha$-hydroxy acid and $\beta$-hydroxy acid; blood circulation accelerators such as $\gamma$-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, glycyrrhiza extract, capsicum tincture, hinokitiol, iodized garlic extract, pyridoxine hydrochloride, DL-$\alpha$-tocopherol, DL-$\alpha$-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, $\gamma$-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SADANISHIKI extract.

(10) Specific Examples of Antioxident

Sodium hydrogensulfite, sodium sulfite, erythorbic acid, sodium erythorbate, dilauryl thiodipropionate, tocopherol, tolylbiguanide, nordihydroguaiaretic acid, parahydroxy anisole, butylhydroxy anisole, dibutylhydroxy toluene, ascorbyl stearate, ascorbyl palmitate, octyl gallate, propyl gallate, carotenoid, flavonoid, tannin, lignin, saponin and plant extracts having antioxidant effect, such as apple extract and clove extract.

(11) Specific Examples of Solvent

Purified water, ethanol, lower alcohol, ethers, LPG, fluorocarbon, N-methylpyrrolidone, fluoroalcohol, volatile linear silicone and next generation fleon (such as fluorocarbon, chlorofluorocarbon, CFC).

(Cosmetic Composition)

The cosmetic composition according to the present invention may further contain an existing or known emulsifier or the like in a general concentration.

(Skin Agent)

The skin agent for external application according to the present invention can also be used as a cosmetic material such as skin milk, skin cream, foundation cream, massage cream, cleansing cream, shaving cream, cleansing foam, skin lotion, lotion, pack, shampoo, rinse, hair growing agent, hair nourishment, hair dye, hair conditioner, dentifrice, gargle, permanent waving agent, ointment, bath preparation and body soap.

(Cosmetic Material)

The cosmetic material can be obtained by blending the skin agent for external application according to the present invention with, for example, alcohol such as ethanol or propylene glycol; an antiseptic such as methyl para-hydroxybenzoate, ethyl para-hydroxybenzoate, butyl para-hydroxybenzoate or propyl para-hydroxybenzoate; and a purified water. However, the cosmetic material is not particularly limited to these specific examples.

The cosmetic material according to the present invention is classified, for example, into makeup cosmetics such as foundation, face powder, eye shadow, eyeliner, eyebrow, cheek, lipstick and nail color; basic cosmetics such as milky lotion, cream, lotion, calamine lotion, sun screen agent, suntan agent, after-shave lotion, pre-shave lotion, pack, acne countermeasure cosmetic and essence; hair care cosmetics such as shampoo, rinse, conditioner, hair color, hair tonic, hair setting agent, hair nourishment and permanent waving agent; body powder, deodorant, depilatory, soap, body shampoo, bath preparation, hand soap and perfume. The present invention can be used as respective cosmetic materials.

The shape or form of the cosmetic material according to the present invention is not particularly limited. The cosmetic material may have a conventionally known shape or form such as two-layer structure, water-in-oil emulsion, oil-in-water emulsion, gel, spray, mousse, oil, solid, sheet and powder.

(Use of Ascorbic Acid Derivative)

The ascorbic acid derivative according to the present invention can be used as a medical or pharmaceutical preparation, agrochemical preparation, an animal drug preparation, a food additive and a feed additive. The content of the ascorbic acid derivative may vary depending on use and therefore, cannot be indiscriminately specified. However, the amount applied may appropriately be increased or decreased according to the purpose and use. The amount required as an ascorbic acid may appropriately be adjusted in accordance with the Pharmaceutical Affairs Law, the Law for Control over Agricultural Medicines, the Regulations for Control of Animal Drugs, ETC., and the Food Sanitation Law.

EXAMPLES

The present invention is described in greater detail below by referring to Examples. However, the present invention is not limited to these Examples.

<Example A-1>

L-Ascorbic acid-2-phosphoric acid-6-(2'-hexyldecanoate) sodium salt

In 500 g of 95% sulfuric acid, 131 mmol (35 g) of 2-hexyldecanoic acid was dissolved at 40° C. To the resulting solution, 146 mmol (50 g) of L-ascorbic acid-2-phosphate sodium salt was added and uniformly stirred for 6 hours. The thus obtained mixture was left standing at room temperature for 24 hours, and thereafter the reaction mixture was poured into 780 g of ice water and the resultant precipitate was extracted with 590 g of methyl-tert-butyl ether. To the resultant ether solution, 590 g of 13% brine was added and then a 20%-aqueous sodium hydroxide solution was added until the pH of the mixture became about 8. The methyl-tert-butyl ether layer was separated by a separating funnel and 300 g of methanol was added to the methyl-tert-butyl ether layer, whereby precipitate was deposited. This precipitate was separated by centrifugation, washed with a small amount of methanol and then dried under reduced pressure, to obtain 21 g of L-ascorbic acid-2-phosphoric acid-6-(2'-hexyldecanoate) sodium salt in a powder form (yield: 27%).

The structure was identified by the nuclear magnetic resonance spectrum.

$^1$H NMR (270 MHz, D$_2$O; $^1$H NMR apparatus, trade name: JNM-EX270, mfd. by Nihon Denshi K.K. (JEOL Ltd.)) δ: 0.89 ppm (t, 6H, J=6.6 Hz), 1.30–1.63 (b, 24H), 2.45 (hep, 1H, J=6.6 Hz), 4.20–4.35 (m, 3H), 4.47 (s, 1H) $^{13}$C NMR (67.8 MHz, D$_2$O; $^{13}$C NMR apparatus, trade name: JNM-EX270, mfd. by Nihon Denshi K.K.) δ: 16.4 ppm (s, 1C), 25.0 (s, 1C), 25.2 (s, 1C), 29.4 (s, 1C), 29.6 (s, 1C), 31.5 (s, 1C), 31.9 (s, 1C), 32.1 (s, 1C), 34.0 (s, 1C), 34.5 (s, 1C), 47.6 (s, 1C), 67.6 (s, 1C), 69.6 (s, 1C), 80.8 (s, 1C), 115.3 (d, 1C, J=7.3 Hz), 178.2 (s, 1C), 179.4 (s, 1C), 180.4 (s, 1C) $^{31}$P NMR (109 MHz, D$_2$O; $^{31}$P NMR apparatus, trade name: JNM-EX270, mfd. by Nihon Denshi K.K.) δ: 4.3 ppm Example A-2

L-Ascorbic acid-2-phosphoric acid-6-(2'-n-heptylundecanoate) sodium salt

The procedure was repeated in the same manner as in Example A-1, except for using 2-n-heptylundecanoic acid according to the present invention in place of 2-hexyldecanoic acid used in Example A-1, to obtain 16 g of L-ascorbic acid-2-phosphoric acid-6-(2'-n-heptylundecanoate) sodium salt in a powder form (yield: 26%).

The structure was identified by the nuclear magnetic resonance spectrum.

$^1$H NMR (270 MHz, D$_2$O) δ: 0.89 ppm (t, 6H, J=6.6 Hz), 1.30–1.63 (b, 24H), 2.43 (hep, 1H, J=6.3 Hz), 4.18–4.36 (m, 3H), 4.57 (s, 1H) $^{13}$C NMR (67.8 MHz, D$_2$O) δ: 16.5 ppm (s, 1C), 25.2 (s, 1C), 25.3 (s, 1C), 29.5 (s, 1C), 29.6 (s, 1C), 31.6 (s, 1C), 31.9 (s, 1C), 32.1 (s, 1C), 32.3 (s, 1C), 33.9 (s, 1C), 34.4 (s, 1C), 34.6 (s, 1C), 47.5 (s, 1C), 67.2 (s, 1C), 69.4 (s, 1C), 80.3 (s, 1C), 115.8 (d, 1C, J=6.1 Hz), 173.8 (s, 1C), 178.3 (d, 1C, J=3.7 Hz), 179.9 (s, 1C) $^{31}$P NMR (109 MHz, D$_2$O) δ: 4.1 ppm Test Example A-1

The L-ascorbic acid-2-phosphoric acid-6-(2'-hexyldecanoate) sodium salt obtained in Example A-1 was dissolved in purified water so as to provide to a concentration of 2 mass %, and the thus obtained solution was charged into a glass bottle with a lid and left standing at 40° C. (under light-shielding condition) for 10 days. The ratio of the compound remaining after the storage was analyzed by using a high-performance liquid chromatograph equipped with Shodex (registered trademark of Showa Denko K.K.) SB802.5 HQ (mfd. by Showa Denko K.K.) column.

(Measurement Conditions for High-Performance Liquid Chromatography)

| | |
|---|---|
| Column: | Shodex (registered trademark of Showa Denko K.K.) OHpak SB802.5 HQ |
| Temperature: | 40° C. |
| Eluent: | 0.03 M Na$_2$SO$_4$ + 0.03 M H$_3$PO$_4$/tetrahydrofuran = 1:2 |
| Flow rate: | 0.5 ml/min |

-continued

| | |
|---|---|
| Amount injected: | 20 μL |
| Detection: | UV 270 nm |

Test Example A-2

A stability test was performed in the same manner as in Test Example A-1 except for using the L-ascorbic acid-2-phosphoric acid-6-(2'-n-heptylundecanoate) sodium salt obtained in Example A-2, instead of the L-ascorbic acid-2-phosphoric acid-6-(2'-hexyldecanoate) sodium salt obtained in Example A-1.

Comparative Example A-1

A stability test was performed in the same manner as in Test Example A-1 except for using an L-ascorbic acid-2-phosphoric acid-6-palmitatic acid ester sodium salt which had been prepared by using the procedure as described in Patent Document 5 (JP-A-10-298174) appearing hereinbefore, instead of the L-ascorbic acid-2-phosphoric acid-6-(2'-hexyldecanoate) sodium salt obtained in Example A-1.

Comparative Example A-2

A stability test was performed in the same manner as in Test Example A-1 except for using an L-ascorbic acid-2-phosphate sodium salt (mfd. by Showa Denko K.K.) having excellent stability, instead of the L-ascorbic acid-2-phosphoric acid-6-(2'-hexyldecanoate) sodium salt obtained in Example A-1.

The results obtained in the above Examples, Comparative Examples, and Test Examples are shown together in the following Table 1.

TABLE 1

| | Ascorbic Acid Derivative | Residual Ratio (%) |
|---|---|---|
| Example A-1 | L-ascorbic acid-2-phosphoric acid-6-(2'-hexyldecanoate) sodium salt | 95.3 |
| Example A-2 | L-ascorbic acid-2-phosphoric acid-6-(2'-n-heptylundecanoate) sodium salt | 95.5 |
| Comparative Example A-1 | L-ascorbic acid-2-phosphoric acid-6-palmitatic acid ester sodium salt | 88.6 |
| Comparative Example A-2 | L-ascorbic acid-2-phosphate sodium salt | 96.9 |

Formulation examples of cosmetic materials are shown below. In these examples, "%", means mass %.

Formulation Example A-1

Cream (1):

| | |
|---|---|
| Condensed hexaglyceryl ricinoleate | 1.0% |
| Fine grain titanium oxide | 5.0% |
| 2-Octyldodecyl pivalate | 8.0% |
| Glyceryl tri(caprylate-caprate) | 3.0% |
| Methylphenylpolysiloxane | 7.0% |
| Decamethylcyclopentasiloxane | 2.0% |
| Cetanol | 2.0% |
| 2-Ethylhexyl para-methoxycinnamate | 6.0% |
| 4-tert-Butyl-4-methoxybenzoylmethane | 2.0% |

-continued

| | |
|---|---|
| Decaglyceryl monoisostearate | 3.0% |
| Xanthane gum | 0.3% |
| L-Ascorbic acid-2-phosphoric acid-6-(2'-hexyldecanoate) sodium salt | 4.0% |
| Purified water in an amount so as to provide a total amount of 100% | |

Formulation Example A-2

Cream (2):

| | |
|---|---|
| Condensed hexaglyceryl ricinoleate | 1.0% |
| 2-Octyldodecyl pivalate | 8.0% |
| Glyceryl tri(caprylate-caprate) | 3.0% |
| Methylphenylpolysiloxane | 7.0% |
| Decamethylcyclopentasiloxane | 2.0% |
| Cetanol | 2.0% |
| Decaglyceryl monoisostearate | 3.0% |
| Xanthane gum | 0.3% |
| L-Ascorbic acid-2-phosphoric acid-6-(2'-n-heptylundecanoate) sodium salt | 4.0% |
| Purified water in an amount so as to provide a total amount of 100% | |

Formulation Example A-3

Skin Lotion:

| | |
|---|---|
| L-Ascorbic acid-2-phosphoric acid-6-(2'-n-heptylundecanoate) sodium salt | 4.0% |
| Citric acid | 0.016% |
| Sodium citrate | 2.0% |
| 1,3-Butylene glycol | 3.0% |
| Ethanol | 3.0% |
| Purified water in an amount so as to provide a total amount of 100% | |

(Production Process)

The above ingredients were dissolved in purified water under heating at 50° C., and the resulting solution was cooled under stirring. Then the stirring was stopped when the temparature became 30° C., and the thus obtained solution was left standing.

Formulation Example A-4

Milky Lotion:

| | |
|---|---|
| L-Ascorbic acid-2-phosphoric acid-6-(2'-hexyldecanoate) sodium salt | 4.0% |
| Glycerin | 8.0% |
| Butylene glycol | 2.0% |
| Hydrogenated lecithin | 0.1% |
| Sodium hyaluronate | 0.05% |
| Hydroxy ethyl cellulose | 0.3% |
| Xanthane gum | 0.3% |
| Sodium citrate | 1.0% |
| Polyethylene glycol-50 hydrogenated caster oil | 0.5% |
| Methylparaben | 0.2% |

-continued

| Purified water in an amount so as to provide a total amount of 100% |
|---|

(Production Process)

The above ingredients except for L-ascorbic acid-2-phosphoric acid-6-(2'-hexyldecanoate) sodium salt were dissolved in purified water under heating at 80° C., the resulting solution was cooled under stirring. Then, L-ascorbic acid-2-phosphoric acid-6-(2'-hexyldecanoate) sodium salt was gradually added to the resultant solution at 50° C. under stirring, the stirring was stopped when the temparature became 40 to 35° C., and the thus obtained solution was left standing.

Example B-1

To the surface of a human skin tissue three-dimensional model (trademark: TESTSKIN LSD-d, mfd. by Toyobo Co., Ltd.), 40 μL of a solution which had been obtained by dissolving each of the substances (1) to (3) to be tested in Dulbecco PBS (−), and the resultant skin tissue model was cultured at 37° C. in the presence of 5% $CO_2$ for two hours. Then, the test solution was removed by aspiration, and thereafter the skin tissue model was cultured at 37° C. in the presence of 5% $CO_2$ for 2, 6 and 12 hours, respectively.

Each of the portions of the skin model which had been sampled at each culture time was washed with Dulbecco PBS (−), the surface portion was punched out by using a punch having a diameter of 6 mm ϕ, and homogenized in a HEPES buffer solution (pH 7.2) to obtain a homogenate. By use of the thus obtained homogenate, the amount of the ascorbic acid contained in the skin model was quantitatively analyzed by using a high performance liquid chromatography. The protein content in the skin model was quantitatively analyzed by using the Lowry method.

1) 2% ascorbic acid-2-phosphate sodium salt
2) 0.5% ascorbic acid-2-phosphoric acid-6-(2'-hexyldecanoate) sodium salt
3) 0.5% ascorbic acid-2-phosphoric acid-6-(2'-n-heptyl undecanoate) sodium salt Measurement Conditions for High Performance Liquid Chromatography <Ascorbic Acid>

| Column: | Shodex (Showa Denko K.K., registered trademark) Asahipak NH2P-50 4E |
|---|---|
| Temperature: | 40° C. |
| Eluent: | acetonitrile: 60 mM $H_3PO_4$ = 80:20 |
| Flow rate: | 0.8 ml/min |
| Detection: | UV 245 nm |

As a result, the amount of the ascorbic acid at each culture time (unit: nmol/mg skin protein) was as follows.

| | 2 hours after culture | 6 hours after culture | 12 hours after culture |
|---|---|---|---|
| 1) | 30 | 24 | 5 |
| 2) | 6 | 10 | 23 |
| 3) | 5 | 11 | 26 |

As shown by the above results, it was found that when the ascorbic acid-2-phosphoric acid-6-(2'-hexyl decanoate) sodium salt or 0.5% ascorbic acid-2-phosphoric acid-6-(2'-n-heptyl undecanoate) sodium salt was administered to the skin model, the concentration of the ascorbic acid in the tissue could easily be enhanced effectively so as to provide a concentration which is effective for accelerating the collagen synthesis, for a long period from the point immediately after the administration.

Example B-2

The collagen synthesis-accelerating effects of the following 1) to 3) test substances was compared with each other, by using a guinea pig model system having an incised (or cut) wound. The base material for dissolving each test substance was purified water containing 20% of ethanol, and 3% of propylene glycol.

1) 2% ascorbic acid-2-phosphate sodium salt
2) 1% ascorbic acid-2-phosphoric acid-6-(2'-hexyl decanoate) sodium salt
3) 1% ascorbic acid-2-phosphoric acid-6-(2'-n-heptyl undecanoate) sodium salt In this experiment, two incised wounds each having a length of 2 cm were formed on the back of a guinea pig by using a scalpel, so that the incised wounds are positioned symmetrically with regard to the center portion of the back. Then, 0.2 ml of the test substance solution was administered thereto twice a day, for four days. After the last administration was completed, a skin piece of 2 cm×2 cm (square shape) was surgically removed from the back of the guinea pig, so that the incised wound portions were positioned substantially at the center of the skin piece. Then, the tension required for the detachment of the incised wound surface was measured. Five guinea pigs were used with respect to one kind of the test substances.

After the measurement of the above tension, a skin section was taken out from the skin piece, so that the incised wound portion was contained in the skin section and the section had a width of 5 mm on both sides of the incised wound portion (i.e., the thus obtained skin section had a total width of 10 mm). The resultant skin section was homogenized in 0.5 M acetic acid so as to provide a homogenate. Two parts by volume of a mixture of diethyl ether-ethanol (volume ratio=1:3) was added to one part by volume of the homogenate solution, and mixed therewith under stirring, and the solvent layer was removed therefrom after centrifugation. Pepsin (mfd. by Wako Pure Chemical Industries, Ltd.) was added to the resultant solvent layer, and was reacted with the solvent layer at 15° C. for 16 hours. After the separation thereof by centrifugation, the resultant supernatant was freeze-dried. The protein content of the thus obtained skin sample was hydrolyzed with hydrochloric acid, and was subjected to amino acid analysis by use of AccQ•Tag Amino acid Analyzer (mfd. by Waters Co.).

The results of the detachment tension measurement for the incised wound portion to which each test substance had been applied, and the hydroxyproline content thereof were as follows. Herein, the hydroxyproline is a substance which can be taken as an index of collagen.

|    | Detachment tension (g/cm) | Hydroxyproline content (nmol/skin wet weight) |
|----|---------------------------|-----------------------------------------------|
| 1) | 123                       | 32.1                                          |
| 2) | 181                       | 38.5                                          |
| 3) | 187                       | 37.6                                          |

As shown by the above results, it was found that the administeration of each of the ascorbic acid-2-phosphoric acid-6-(2'-hexyl decanoate) sodium salt or ascorbic acid-2-phosphoric acid-6-(2'-n-heptyl undecanoate) sodium had an effect of accelerating the collagen synthesis so as to promote the recovery of the incised wound surface.

Formulation Example B-1

Skin Lotion

| | |
|---|---|
| Ascorbic acid-2-phosphoric acid-6-(2'-hexyl decanoate) sodium salt | 2.0% |
| Citric acid | 0.016% |
| Sodium citrate | 2.0% |
| 1,3-butylene glycol | 3.0% |
| Ethanol | 3.0% |
| Purified water in an amount so as to provide a total amount of 100% | |

(Production Process)

The above ingredients were dissolved in purified water under warming at 50° C., and the resultant mixture was cooled under stirring. When the temperature of the mixture became 30° C., the stirring was stopped, and the mixture was left standing.

Formulation Example B-2

Skin Lotion

| | |
|---|---|
| Ascorbic acid-2-phosphoric acid-6-(2'-n-heptyl undecanoate) sodium salt | 2.0% |
| Citric acid | 0.016% |
| Sodium citrate | 2.0% |
| 1,3-butylene glycol | 3.0% |
| Ethanol | 3.0% |
| Purified water in an amount so as to provide a total amount of 100% | |

(Production Process)

The above ingredients were dissolved in purified water under warming at 50° C., and the resultant mixture was cooled under stirring. When the temperature of the mixture became 30° C., the stirring was stopped, and the mixture was left standing.

Formulation Example B-3

Cream:

| | |
|---|---|
| Ascorbic acid-2-phosphoric acid-6-(2'-hexyl decanoate) sodium salt | 2.0% |
| Cetanol | 5.0% |
| Cyclomethicone | 4.0% |
| Cetyl octanoate | 4.0% |
| Trioctanoin | 2.0% |
| Palmityl alcohol | 1.0% |
| Dimethicone | 0.3% |
| Butylene glycol | 7.0% |
| Hydrogenated lecithin | 1.0% |
| Myristic acid poly glyceryl-10 | 1.0% |
| Sodium citrate | 2.0% |
| Methyl paraben | 0.15% |
| Propyl paraben | 0.05% |
| Xanthan gum | 0.1% |
| Purified water in an amount so as to provide a total amount of 100% | |

(Production Process)

The above ingredients (except for the ascorbic acid-2-phosphoric acid-6-(2'-hexyl decanoate) sodium salt) were dissolved in purified water under warming at 80° C., and the resultant mixture was cooled under stirring. At 50° C., the ascorbic acid-2-phosphoric acid-6-(2'-hexyl decanoate) sodium salt was gradually added to this mixture. When the temperature of the mixture became 35–30° C., the stirring was stopped, and the mixture was left standing.

Formulation Example B-4

Cream:

| | |
|---|---|
| Ascorbic acid-2-phosphoric acid-6-(2'-n-heptyl undecanoate) sodium salt | 2.0% |
| Cetanol | 5.0% |
| Cyclomethicone | 4.0% |
| Cetyl octanoate | 4.0% |
| Trioctanoin | 2.0% |
| Palmityl alcohol | 1.0% |
| Dimethicone | 0.3% |
| Butylene glycol | 7.0% |
| Hydrogenated lecithin | 1.0% |
| Myristic acid poly glyceryl-10 | 1.0% |
| Sodium citrate | 2.0% |
| Methyl paraben | 0.15% |
| Propyl paraben | 0.05% |
| Xanthan gum | 0.1% |
| Purified water in an amount so as to provide a total amount of 100% | |

(Production Process)

The above ingredients (except for the ascorbic acid-2-phosphoric acid-6-(2'-n-heptyl undecanoate) sodium salt) were dissolved in purified water under warming at 80° C., and the resultant mixture was cooled under stirring. At 50° C., the ascorbic acid-2-phosphoric acid-6-(2'-n-heptyl undecanoate) sodium salt was gradually added to this mixture. When the temperature of the mixture became 35–30° C., the stirring was stopped, and the mixture was left standing.

Formulation Example B-5

Milky Lotion:

| | |
|---|---|
| L-Ascorbic acid-2-phosphoric acid-6-(2'-hexyldecanoate) sodium salt | 2.0% |
| Glycerin | 8.0% |
| Butylene glycol | 2.0% |
| Hydrogenated lecithin | 0.1% |
| Sodium hyaluronate | 0.05% |
| Hydroxy ethyl cellulose | 0.3% |
| Xanthane gum | 0.3% |
| Sodium citrate | 1.0% |
| Polyethylene glycol-50 hydrogenated caster oil | 0.5% |
| Methylparaben | 0.2% |
| Purified water in an amount so as to provide a total amount of 100% | |

(Production Process)

The above ingredients except for L-ascorbic acid-2-phosphoric acid-6-(2'-hexyldecanoate) sodium salt were dissolved in purified water under heating at 80° C., the resulting solution was cooled under stirring. Then, L-ascorbic acid-2-phosphoric acid-6-(2'-hexyldecanoate) sodium salt was gradually added to the resultant solution at 50° C. under stirring, the stirring was stopped, when the temparature became 40 to 35° C., and the thus obtained solution was left standing.

Formulation Example B-6

| | |
|---|---|
| L-Ascorbic acid-2-phosphoric acid-6-(2'-heptyl undecanoate) sodium salt | 2.0% |
| Glycerin | 8.0% |
| Butylene glycol | 2.0% |
| Hydrogenated lecithin | 0.1% |
| Sodium hyaluronate | 0.05% |
| Hydroxy ethyl cellulose | 0.3% |
| Xanthane gum | 0.3% |
| Sodium citrate | 1.0% |
| Polyethylene glycol-50 hydrogenated caster oil | 0.5% |
| Methylparaben | 0.2% |
| Purified water in an amount so as to provide a total amount of 100% | |

(Production Process)

The above ingredients except for L-ascorbic acid-2-phosphoric acid-6-(2'-heptyl undecanoate) sodium salt were dissolved in purified water under heating at 80° C., the resulting solution was cooled under stirring. Then, L-ascorbic acid-2-phosphoric acid-6-(2'-heptyl undecanoate) sodium salt was gradually added to the resultant solution at 50° C. under stirring, the stirring was stopped, when the temperature became 40 to 35° C., and the thus obtained solution was left standing.

Example C-1 (Whitening)

The quantities in the compositions in Examples appearing hereinafter are described in terms of mass % (wt. %).

Lotion (1)

The following ingredients 1) to 4) were uniformly dispersed and dissolved with each other so as to provide the following final concentrations. The resultant mixture was added to the ingredient 5) under stirring, to obtain Lotion (1).

| | |
|---|---|
| 1) Ascorbic acid-2-phosphoric acid-6-(2'-hexyl decanoate) sodium salt | 2.00 |
| 2) Ethanol | 5.00 |
| 3) Propylene glycol | 5.00 |
| 4) Methyl para-hydroxy benzoate | 0.20 |
| 5) Purified water | 87.8 |

Lotions (2) to (4)

Lotions (2) to (4) were prepared in the same manner as in the production of Lotion (1), except that each of the following ingredient was respectively used so as to provide the same concentration, instead of the ingredient (1) of Lotion (1).

Lotion (2):
Ascorbic acid-2-phosphoric acid-6-(2'-n-heptyl undecanoate) sodium salt Lotion (3) (Comparative Control Reference):
Ascorbic acid-2-phosphoric acid sodium salt Lotion (4) (Negative Control):
Purified water In each of the above lotions, the ingredients were uniformly dissolved, and all of the lotions showed a good stability with the elapse of time.

Example C-2

Lotion (5)

The following ingredients 1) to 4) were uniformly dispersed and dissolved with each other so as to provide the following final concentrations. The resultant mixture was added to the ingredient 5) under stirring, to obtain Lotion (5).

| | |
|---|---|
| 1) Ascorbic acid-2-phosphoric acid-6-(2'-hexyl decanoate) sodium salt | 0.10 |
| 2) Ethanol | 5.00 |
| 3) Propylene glycol | 5.00 |
| 4) Methyl para-hydroxy benzoate | 0.20 |
| 5) Purified water | 89.7 |

Lotions (6) to (8)

Lotions (6) to (8) were prepared in the same manner as in the production of Lotion (5), except that each of the following ingredient was respectively used so as to provide the same concentration, instead of the ingredient (1) of Lotion (5).

Lotion (6):
Ascorbic acid-2-phosphoric acid-6-(2'-n-heptyl undecanoate) sodium salt Lotion (7) (Comparative Control Reference):
Ascorbic acid-2-phosphoric acid sodium salt Lotion (8) (Negative Control):
Purified water In each of the above lotions, the ingredients were uniformly dissolved, and all of the lotions showed a good stability with the elapse of time.

Example C-3

Gel-Type Preparation (1) for External Use

The following ingredient 1) was uniformly dispersed in the following ingredient 2) so as to provide the following final concentration, and the resultant mixture was added to the ingredient 3) under stirring, to obtain an intended gel-type external preparation (1).

| | |
|---|---|
| 1) Ascorbic acid-2-phosphoric acid-6-(2'-hexyl decanoate) sodium salt | 10 |
| 2) glycerol | 20 |
| 3) Octyl dodecyl myristate | 70 |

Gel-Type Preparations (2) to (4) for External Use

Gel-type external preparations (2) to (4) were prepared in the same manner as in the production of gel-type external preparation (1), except that each of the following ingredient was respectively used so as to provide the same concentration, instead of the ingredient (1) of Gel-type preparation (1).

Gel-Type Preparation (2):
 Ascorbic acid-2-phosphoric acid-6-(2'-n-heptyl undecanoate) sodium salt Gel-Type Preparation (3) (Comparative Control Reference):
 Ascorbic acid-2-phosphoric acid sodium salt Gel-Type Preparation (4) (Negative Control):
 Purified water In each of the above gel-type external preparations, the ingredients were uniformly dissolved, and all of the gel-type external preparations showed a good stability with the elapse of time.

Example C-4

(Effect of Preventing Pigmentation)

The hair of the entire surface on the back of each of seven weeks-aged 30 male Wizer-Maple guinea pigs (WM, SPF) was trimmed by using electric hair clippers (0.05 mm blade), and then the surface was shaven by using an electric shaver. Thereafter, the back surface was covered with an adhesive stretchable bandage (Silky-tex, the outside of which was covered with an aluminum foil) having four opening windows each having a size of 1.5 cm×1.5 cm. With respect to the respective windows, each of Lotions (1) to (8) and Gel-type external preparations (1) to (4) which had been prepared in Examples C-1 to C-3, was sequentially applied to ten sites each in an amount of 0.05 ml. After four hours from the application of the preparations, the dosage sites were washed with water by using absorbent cotton impregnated with water, and then dried. Then, each of the animals was fixed onto a retention device, and the respective sites were irradiated with medium-wavelength ultraviolet ray (UVB) at a radiant exposure of 300 mJ/cm$^2$ with a distance of about 10 cm by using ultraviolet ray-irradiating device (mfd. by Shinano Seisakusho, Toshiba FL40S/E30-type fluorescent lamp, equipped with six SE lamps). After the irradiation, each of the same Lotions (1) to (8) and Gel-type external preparations (1) to (4) was again applied to the corresponding sites each in an amount of 0.05 ml.

These procedure was repeated for three days. After 14 days from the last irradiation, the degree of the resultant pigmentation (or chromatosis) was determined according to the following acceptance criteria in terms of scores. Further, the brightness of the skin was determined by using a color-difference meter (MINOLTA, CR-20) with respect to the four corners and central portion of each of the dosage/irradiation sites (total five sites). With respect to each of the preparations, the effect of preventing the pigmentation was judged from the average of score values (ten data for each preparation) and the average of brightness values (50 data for each preparation).

Acceptance Criteria for Pigmentation
 No pigmentation was recognized: Score 0 (zero)
 Slight pigmentation was recognized: Score 1
 Low-degree pigmentation was recognized: Score 2
 Middle-degree pigmentation was recognized: Score 3
 High-degree pigmentation was recognized: Score 4

Results (Average)

| Preparation | Score | Brightness |
|---|---|---|
| Lotion (1) | 0.8 | 63.0 |
| Lotion (2) | 1.0 | 61.1 |
| Lotion (3) | 2.1 | 61.8 |
| Lotion (4) | 3.0 | 59.5 |
| Lotion (5) | 2.0 | 61.7 |
| Lotion (6) | 2.2 | 62.1 |
| Lotion (7) | 3.0 | 59.9 |
| Lotion (8) | 3.0 | 60.1 |
| Gel-type ext. prep. (1) | 0.5 | 63.5 |
| Gel-type ext. prep. (2) | 0.8 | 62.8 |
| Gel-type ext. prep. (3) | 1.2 | 62.1 |
| Gel-type ext. prep. (4) | 3.0 | 59.9 |

As described above, it was found that any of the lotions and gel-type external preparations containing the ascorbic acid derivative according to the present invention showed an excellent effect of preventing the pigmentation.

Example C-5

(Effect of Removing Pigmentation)

The hair of the entire surface on the back of each of six weeks-aged 30 male Wizer-Maple guinea pigs (WM, SPF) was trimmed by using electric hair clippers (0.05 mm blade), and then the surface was shaven by using an electric shaver. Thereafter, the back surface was covered with an adhesive stretchable bandage (Silky-tex, the outside of which was covered with an aluminum foil) having four opening windows each having a size of 1.5 cm×1.5 cm. Then, each of the animals was fixed onto a retention device, and the respective sites were irradiated with medium-wavelength ultraviolet ray (UVB) at a radiant exposure of 750 mJ/cm$^2$ with a distance of about 10 cm by using ultraviolet ray-irradiating device (mfd. by Shinano Seisakusho, Toshiba FL40S/E30-type fluorescent lamp, equipped with six SE lamps). In a period of from four days after the irradiation to 28 days after the irradiation, twice a day (in the morning and in the evening), with respect to the respective windows, each of Lotions (1) to (8) and Gel-type external preparations (1) to (4) which had been prepared in Examples C-1 to C-3, was sequentially applied to ten sites each in an amount of 0.05 ml. After 28 days from the last irradiation, the degree of the resultant pigmentation was determined according to the acceptance criteria in terms of scores, in the same manner as in Example C-4. With respect to each of the preparations, the effect of removing the pigmentation was judged from the average of score values (ten data for each preparation).

Results (Average)

| Preparation | Score |
|---|---|
| Lotion (1) | 2.2 |
| Lotion (2) | 2.4 |
| Lotion (3) | 3.3 |
| Lotion (4) | 3.5 |
| Lotion (5) | 2.9 |
| Lotion (6) | 3.0 |
| Lotion (7) | 3.5 |
| Lotion (8) | 3.8 |
| Gel-type ext. prep. (1) | 2.2 |
| Gel-type ext. prep. (2) | 2.5 |
| Gel-type ext. prep. (3) | 2.9 |
| Gel-type ext. prep. (4) | 3.5 |

As described above, it was found that any of the lotions and gel-type external preparations containing the ascorbic acid derivative according to the present invention showed a distinct effect of removing the pigmentation.

Example D-1

5 kg of basic ingredients comprising 43 mass % of cuttlefish meal, 15 mass % of lobster (or shrimp) meal, 10 mass % of fish meal, 10 mass % of crude (non-refined) fish oil (mfd. by Nippon Suisan K.K.), 10 mass % of beer yeast, 3 mass % of active gluten, 2 mass % of starch, 2 mass % of ascorbic acid-2-phosphoric acid-6-(2'-hexyl decanoate) sodium salt prepared in Example A-1, and 5 mass % of mineral mixture, was subjected to mixing. Then, the moisture content of the thus obtained mixture was adjusted so as to provide a moisture content of 45%. The mixture was extruded by using an extruder so as to provide a product temperature of 115° C., then dried by a dryer so as to provide a moisture content of about 10%, to obtain pellets of feeding stuff.

Comparative Example D-1

Pellets of feeding stuff were prepared in the same manner as in Example D-1 except for using no ascorbic acid-2-phosphoric acid-6-(2'-hexyl decanoate) sodium salt.

Comparative Example D-2, Example D-3

Feeding tests were conducted by using rainbow trouts. 20 rainbow trouts (average fish weight: 0.79 kg) were provided, and accommodated in two compartments of a circulation and filtration-type water tank, so that each compartment accommodated 10 rainbow trouts. With respect to these rainbow trouts, feeding tests were conducted by using the feeding stuff which had been prepared in Example D-1. Herein, the feeding stuff which had been prepared in Comparative Example D-1 was fed to the compartment for control test. The water temperature of the feeding period was adjusted to 18° C. and the feeding rate was set to 4% per the fish weight. After the termination of the feeding test, all of the ten fish was taken out, and the fish weights thereof were measured. With respect to the rainbow trouts of test area, the average fish weight became 0.85 kg, while the average fish weight of the control area became 0.82 kg.

From the above results, the effect of ascorbic acid-2-phosphoric acid-6-(2'-hexyl decanoate) sodium salt according to the present invention was recognized.

Example E-1

25 g of bees wax (mfd. by Noda wax Co., Ltd., melting point 60° C.) was added to 1 kg of egg yolk lecithin (mfd. by Kewpie Co., Ltd., trade name "PL-30", PC content about 25%), and the resulting mixture was stirred under warming at about 70° C. until a uniform mixture was formed. This conditions were maintained for five minutes, and then cooled. Subsequently, 25 g of the ascorbic acid-2-phosphoric acid-6-(2'-hexyl decanoate) sodium salt prepared in Example A-1 was added, and the resulting mixture was stirred until a uniform mixture was formed to obtain a mixture. On the other hand, 2 kg of gelatine, 1 kg of glycerol, and 1.5 kg of water were sufficiently mixed with each other and the resultant mixture was shaped into a sheet. Two pieces of the thus formed gelatine sheet ware set to a rotary type capsule forming machine, and the above mixture was injected in an amount of 300 mg per one capsule. The injection port of each capsule was sealed up under pressure to produce 3500 capsules.

INDUSTRIAL APPLICABILITY

The novel ascorbic acid derivative to be produced by the production process according to the present invention is liable to be incorporated into cells, and therefore it can elevate the cumulative concentration of ascorbic acid in cells, even when it is administrated into the cells in a small amount. In addition, this ascorbic acid derivative has an improved storage stability, as compared with conventional ascorbic acid derivatives. Accordingly, the ascorbic acid derivative according to the present invention can be widely used for various preparations such as vitamin C preparations, skin preparations for external use, medical or pharmaceutical preparations, agrochemical preparations, animal drug preparations, food additives, and feed additives, which contain an ascorbic acid derivative as an effective ingredient.

In addition, when the ascorbic acid derivative according to the present invention is incorporated into a cosmetic for preventing wrinkles, etc., the ascorbic acid derivative has an excellent effect of accelerating the collagen synthesis, and an excellent effect of suppressing the collagen decomposition, so that it can prevent or improve a change in the form or shape skin due to aging. Accordingly, the ascorbic acid derivative according to the present invention is widely applicable to medical or pharmaceutical preparations, quasi-drug products, cosmetics, etc.

What is claimed is:

1. An ascorbic acid derivative, which is a compound represented by the following general formula (1) or a salt thereof:

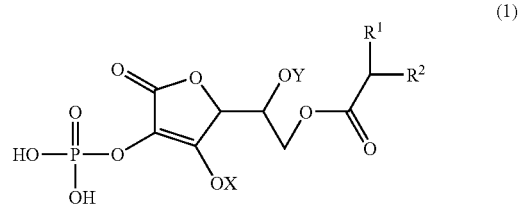

(wherein X and Y each represents H or a protective group for OH, $R^1$ and $R^2$ each represents an alkyl group having from 1 to 19 carbon atoms, which may be linear or branched, and the total number of carbon atoms in $R^1$ and $R^2$ is an integer of 5 to 22).

2. The ascorbic acid derivative according to claim 1, which is a salt with one or more metal selected from the group consisting of alkali metal, alkaline earth metal, aluminum, iron, zinc and bismuth.

3. The ascorbic acid derivative according to claim 1, which is a salt with ammonia, monoethanolamine, diethanolamine, triethanolamine, dicyclohexylamine or 2-amino-1-methylpropanol.

4. The ascorbic acid derivative according to any one of claims 1 to 3, wherein the total number of carbon atoms in $R^1$ and $R^2$ of the general formula (1) is an integer of 8 to 18.

5. The ascorbic acid derivative according to claim 4, wherein $R_1$ and $R^2$ of the general formula (1) are a linear alkyl group, and the total number of carbon atoms in the linear alkyl groups of $R^1$ and $R^2$ is 14 or 16.

6. The ascorbic acid derivative according to claim 5, wherein in the general formula (1), $R^1$ is n-$C_9H_{19}$ and $R^2$ is n-$C_7H_{15}$; or $R^1$ is n-$C_8H_{17}$ and $R^2$ is n-$C_6H_{13}$.

7. A process for producing an ascorbic acid derivative according to claim 1, comprising a step of reacting a compound represented by the following general formula (2) and/or a salt thereof:

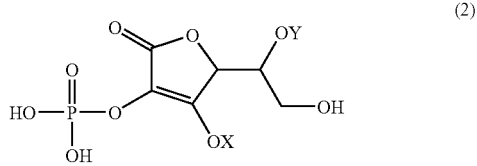

(2)

(wherein X and Y each represents H or a protective group for OH), with at least one selected from fatty acid, fatty acid salt, fatty acid ester, fatty acid halide, and/or fatty acid anhydride.

8. The process for producing an ascorbic acid derivative according to claim 7, wherein the reaction is performed in the presence of a condensing agent and/or dehydrating agent.

9. The process for producing an ascorbic acid derivative according to claim 8, wherein the dehydrating agent is sulfuric acid.

10. The process for producing an ascorbic acid derivative according to any one of claims 7, wherein the reaction is conducted in a solvent selected from the group consisting of: water, acetone, dioxane, toluene, ethylbenzene, methyl-tert-butyl ether and sulfuric acid.

11. A vitamin C preparation comprising a therapeutically effective amount of the ascorbic acid derivative according to claim 1 as an effective ingredient.

12. A composition comprising a therapeutically effective amount of the ascorbic acid derivative according to claim 1, in the form of a medical or pharmaceutical preparation, an agrochemical preparation or an animal drug preparation.

13. A composition comprising a therapeutically effective amount of the ascorbic acid derivative according to claim 1, in the form of a food or feed additive.

* * * * *